(12) United States Patent
Dieleman et al.

(10) Patent No.: US 9,723,834 B2
(45) Date of Patent: Aug. 8, 2017

(54) COMPOSITION CONTAINING A PYRIPYROPENE INSECTICIDE AND A BASE

(75) Inventors: Cedric Dieleman, Scheibenhard (FR); Torsten Knieriem, Mannheim (DE); Michael Krapp, Altrip (DE); Paul Ch. Kierkus, Wake Forest, NC (US); Wen Xu, Cary, NC (US); Kara Benton, Holly Springs, NC (US)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/822,530

(22) PCT Filed: Sep. 13, 2011

(86) PCT No.: PCT/EP2011/065848
§ 371 (c)(1),
(2), (4) Date: Mar. 12, 2013

(87) PCT Pub. No.: WO2012/035010
PCT Pub. Date: Mar. 22, 2012

(65) Prior Publication Data
US 2013/0184153 A1    Jul. 18, 2013

Related U.S. Application Data

(60) Provisional application No. 61/382,513, filed on Sep. 14, 2010, provisional application No. 61/426,538, filed on Dec. 23, 2010.

(30) Foreign Application Priority Data

Sep. 14, 2010 (EP) ..................... 10176608

(51) Int. Cl.
*A01N 53/00* (2006.01)
*A01N 43/90* (2006.01)
*A01N 25/22* (2006.01)

(52) U.S. Cl.
CPC ............. *A01N 25/22* (2013.01); *A01N 43/90* (2013.01); *A01N 53/00* (2013.01)

(58) Field of Classification Search
CPC ........ A01N 43/90; A01N 53/00; A01N 25/22; A01N 2300/00; A01N 25/30
(Continued)

(56) References Cited

U.S. PATENT DOCUMENTS 3,948,636 A   4/1976  Marks
5,089,259 A   2/1992  Wessling et al.
(Continued)

FOREIGN PATENT DOCUMENTS

CA    2 609 527    12/2006
EP    1 889 540    2/2008
(Continued)

OTHER PUBLICATIONS

C.J. Wang and Z.Q. Liu, "Foliar uptake of pesticides—Present status and future challenge", Pesticide Biochemistry and Physiology 87 (2007) 1-8.*
(Continued)

*Primary Examiner* — John Pak
*Assistant Examiner* — Nathan W Schlientz
(74) *Attorney, Agent, or Firm* — Brinks Gilson & Lione

(57) ABSTRACT

The present invention relates to a composition comprising a pyripyropene pesticide of the formula (I) or (II) as defined below

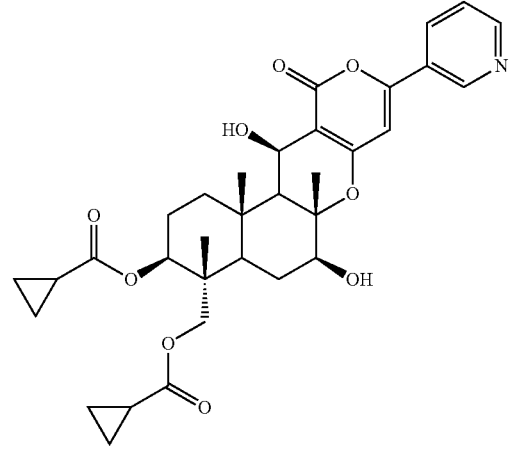

(Formula I)

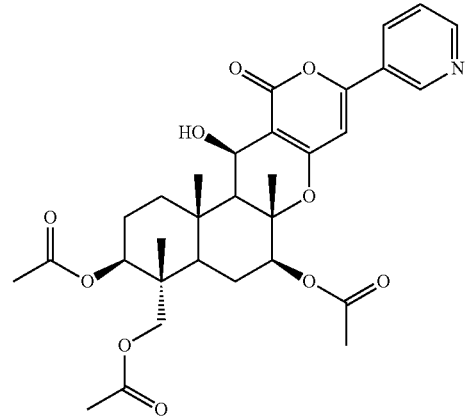

(Formula II)

and a base.
The present invention relates also to methods of preparing and applying such compositions, as well as several uses thereof, and finally seeds, comprising said composition.

27 Claims, No Drawings

(58) Field of Classification Search
USPC .......................................... 504/100; 514/338
See application file for complete search history.

(56) References Cited

U.S. PATENT DOCUMENTS

| | | | |
|---|---|---|---|
| 5,807,721 | A | 9/1998 | Omura et al. |
| 6,495,595 | B2 | 12/2002 | Moore et al. |
| 6,521,785 | B2 | 2/2003 | Shannon et al. |
| 6,706,666 | B2 * | 3/2004 | Hasebe .................. A01N 33/08 424/600 |
| 7,241,454 | B2 | 7/2007 | Warrington et al. |
| 7,268,259 | B1 | 9/2007 | Behler et al. |
| 7,491,738 | B2 | 2/2009 | Goto et al. |
| 2004/0106523 | A1 | 6/2004 | Stridde et al. |
| 2004/0157743 | A1 | 8/2004 | Rosenfeldt et al. |
| 2006/0165748 | A1 | 7/2006 | Arimoto |
| 2008/0096763 | A1 | 4/2008 | Dawson et al. |
| 2008/0300313 | A1 | 12/2008 | Byrne et al. |
| 2008/0312290 | A1 | 12/2008 | Vermeer et al. |
| 2010/0281584 | A1 | 11/2010 | Horikoshi et al. |
| 2013/0184153 | A1 | 7/2013 | Dieleman et al. |
| 2013/0190360 | A1 | 7/2013 | Xu |
| 2014/0142289 | A1 | 5/2014 | Anzai et al. |
| 2014/0371178 | A1 | 12/2014 | Horikoshi et al. |

FOREIGN PATENT DOCUMENTS

| | | |
|---|---|---|
| EP | 2 036 437 | 3/2009 |
| EP | 2 107 060 | 10/2009 |
| EP | 2 119 361 | 11/2009 |
| EP | 2 186 815 | 5/2010 |
| EP | 2 223 599 | 9/2010 |
| JP | 2993767 | 10/1999 |
| JP | 2002-522400 | 7/2002 |
| JP | 2002-532464 | 10/2002 |
| JP | 200815344 | 6/2005 |
| WO | WO 94/09147 | 4/1994 |
| WO | WO 94/09417 | 4/1994 |
| WO | WO 98/35553 | 8/1998 |
| WO | WO 00/07709 | 2/2000 |
| WO | WO 00/35863 | 6/2000 |
| WO | WO 2004/060065 | 7/2004 |
| WO | WO 2006/129714 | 12/2006 |
| WO | WO 2007/117001 | 10/2007 |
| WO | WO 2008/013336 | 1/2008 |
| WO | WO 2008/108491 | 9/2008 |
| WO | WO 2009/081851 | 7/2009 |
| WO | WO 2010010955 | 1/2010 |
| WO | WO 2011/113052 | 9/2011 |
| WO | WO 2011/147952 | 12/2011 |
| WO | WO 2011/147953 | 12/2011 |
| WO | WO 2012/035015 | 3/2012 |
| WO | WO 2013/135604 | 9/2013 |
| WO | WO 2013/135605 | 9/2013 |
| WO | WO 2013/135606 | 9/2013 |
| WO | WO 2013/135610 | 9/2013 |

OTHER PUBLICATIONS

International Search Report dated Oct. 6, 2011, prepared in International Application No. PCT/EP2011/065848.
International Preliminary Report on Patentability dated Dec. 10, 2012, prepared in International Application No. PCT/EP2011/065848.
Sunazuka, Toshiaki, et al., "Synthetic Study of α-Pyrone Meroterpenoids, Pyripyropens", Journal of Society of Synthetic Organic Chemistry, 1998, pp. 478-488, vol. 56, No. 6.
Omura, Satoshi, et al., "Pyripyropense, highly potent inhibitors of Acyl-CoA: Cholesterol Acyltransferase produced by *Aspergillus fumigatus*", Journal of Antibiotics, 1993, p. 1168-9, vol. 46, No. 7.
Wang, Hui-Juan, et al., Aflavinines and Other Antiinsectan Metabolites from the Ascostromata of *Eupenicillium crustaceum* and related Species, Applied and Environmental Microbiology, 1995, p. 4429-35, vol. 61, No. 12.
Office Action dated Sep. 30, 2014 in U.S. Appl. No. 13/822,514.
Narayanan, K.S., et al. "Macro and Microemulsion technology and trands", Pesticide Formulation and Adjuvant Technology, Foy, C.L. and Pritchard, D.W., CRC Press, Boca Raton, FL, 1996, p. 148-164.
Wang, C.J., et al. "Foliar uptake of pesticides—present status and future challenge", Pesticide Biochemistry and Physiology, 2007, p. 1-8, vol. 87.
Final Office Action dated Apr. 2, 2015 in U.S. Appl. No. 13/822,514.
Office Action dated Jul. 13, 2015 in U.S. Appl. No. 14/383,661.
Unknown Author, "Noyaku Seizai Gaido", Japan Plant Protection Association, 1997, pp. 26-31 and 104-112, Pesticide Science Society of Japan, Special Committees on Agricultural Formulation and ApplicationEnglish translation provided.
Office Action dated Jan. 20, 2016 in U.S. Appl. No. 13/822,514.
Office Action dated Apr. 2, 2015 in U.S. Appl. No. 13/822,514.
Office Action dated Sep. 30, 2015 U.S. Appl. No. 14/383,756.
Office Action dated Apr. 20, 2016 U.S. Appl. No. 14/383,756.
Office Action dated Sep. 8, 2016 in U.S. Appl. No. 134/383,665.
Office Action dated Jan. 5, 2017 from U.S. Appl. No. 14/383,731, filed Sep. 8, 2014.
Office Action dated 2017—Mar. 14, 2017 from U.S. Appl. No. 14/383,665, filed Sep. 8, 2014.

* cited by examiner

COMPOSITION CONTAINING A PYRIPYROPENE INSECTICIDE AND A BASE

This application is a National Stage application of International Application No. PCT/EP2011/065848, filed Sep. 13, 2011, which claims the benefit of U.S. Provisional Application No. 61/382,513, filed Sep. 14, 2010; and U.S. Provisional Application No. 61/426,538, filed Dec. 23, 2010, the entire contents of which are hereby incorporated herein by reference. This application also claims priority under 35 U.S.C. §119 to European Patent Application No. 10176608.7, filed Sep. 14, 2010 the entire contents of which is hereby incorporated herein by reference.

The present invention relates to compositions comprising a pyripyropene pesticide as defined below and a base.

When preparing agrochemical formulations of pesticidal compounds different problems can be encounter. One problem may be that the stability of the pesticidal active compound may be affected in the agrochemical formulation, for example especially during storage time. Lack of stability might be particularly problematic in cases, where in the formulation the pesticide compound is present in dissolved form or where the pesticide formulation contains components, which affect the stability of the compound such as water or certain surfactants/adjuvants. Thus one disadvantage of known agrochemical formulations of pesticides is a potentially lower stability of the pesticidal active ingredient in an agrochemical formulation.

One object of the present invention is therefore to find a way to stabilize the pesticide in an agrochemical formulations and to improve, to increase and/or to prolong its storage time in agrochemical formulations.

Especially, it is an object of the present invention to find a way to stabilize insecticidal active pyripyropene derivatives in agrochemical formulations, preferably also at elevated temperatures.

This object was solved by a agrochemical composition comprising a pyripyropene pesticide and a base The composition of the present invention comprises as pesticide a pyripyropene derivative of the formula (I) or of formula (II).

The pyripyropene pesticide of formula (I)

(Formula I)

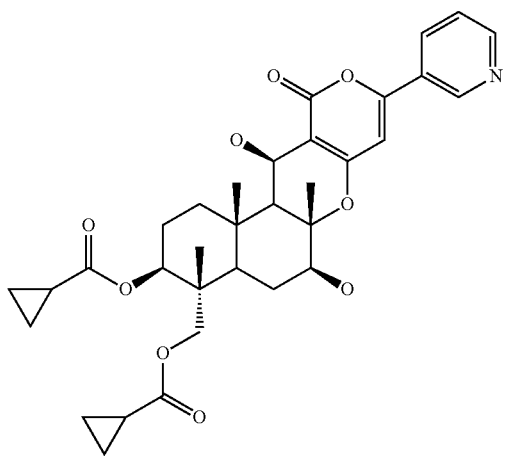

(in the following also called "Insecticide A") is known from WO 2009/081851 (Examples, compound 4) and belongs to the class of pyripyropene derivatives.

WO 2009/081851 discloses various agrochemical formulations of Insecticide A and useful additives for agrochemical formulations of it.

EP 2 119 361 and EP 1 889 540 disclose various agrochemical formulations of pyripyropene derivatives and useful additives for agrochemical formulations of it.

The pyripyropene pesticide of formula (I) may be prepared by the process described in WO 2006/129714 or EP 2 186 815.

Pyripyropene A (formula II herein below), produced e.g. by the method described in Journal of Society of Synthetic Organic Chemistry, Japan (1998), Vol. 56, No. 6, pp. 478-488 or WO 94/09417, may for example be used as starting material for preparing further pyripyropene derivatives.

(Formula II)

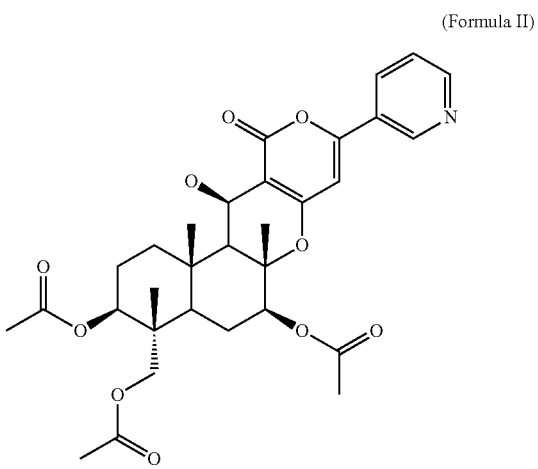

Pyripyropen A of the formula II (in the following also called "Insecticide B") has inhibitory activity against ACAT (acyl-CoA: cholesterol acyltransferase) and is expected to be applied, for example, for the treatment of diseases induced by cholesterol accumulation, as described in Japanese Patent No. 2993767 (Japanese Patent Laid-Open Publication No. 360895/1992) and Journal of Antibiotics (1993), 46(7), 1168-9.

Furthermore, Applied and Environmental Microbiology (1995), 61(12), 4429-35 describes that pyripyropene A ("Insecticide B") itself has insecticidal activity against larvae of *Helicoverpa zea*. Furthermore, WO 2004/060065 describes that pyripyropene A has insecticidal activity against *Plutella xylostella* L larvae and *Tenebrio molitor* L.

When trying to provide agricultural formulations of pyripyropene derivatives, in particular pyripyropene derivatives of formulae I or II, one faces several problems. One problem associated with pyripyropene derivatives of the formulae I and II is their poor stability in agricultural formulations. Lack of stability of the compounds of formulae I or II is particularly problematic in cases, where in the formulation the pesticide compound is present in dissolved form or where the pesticide formulation contains components, which affect the stability of the compound such as water or certain surfactants/adjuvants such as alkoxylated aliphatic alcohols. Another problem one may encounter is that the pesticidal activity of the pesticidal active compound may be affected negatively in some way in the agrochemical formulation.

One object of the present invention is therefore to find a way to stabilize the pyripyropene derivatives of the formulae I and II in an agrochemical formulations. A further object of the present invention is to improve the stability of pyripyropene derivates in liquid formulations, where the pyripyropene derivatives of the formula II are present in dissolved form such as in emulsion concentrates or micro-emulsions. A further object of the present invention is to provide stabilization of the pyripyropene derivatives of the formulae I and II in agricultural compositions, which contain water or certain surfactants/adjuvants.

The improvement of the insecticidal activity of pyripyropene of the formulae I or II in agrochemical formulations is another aspect of the present invention. The development of a novel pest control composition comprising pyripyropene of the formula I or II itself having effective insecticidal activity is desirable. Therefore, it is an object of the present invention to find a way to stabilize, to improve, to increase and/or to prolong the insecticidal activity of pyripyropene derivatives of the formulae I or II.

These and further objects are solved by a agrochemical composition comprising a pyripyropene pesticide of the formulae I or II and at least one base.

The present invention also relates to methods of preparing and applying such compositions, as well as several uses thereof. In particular, the present invention also relates to a method for preparing said composition comprising contacting, in particular mixing, the pyripyropene pesticide of the formulae I or II and the base.

The invention also relates to a method for preparing an aqueous tank-mix comprising the steps of a) providing a composition containing the pyripyropene pesticide of the formulae I or II; b) providing a composition containing the base; and c) contacting the compositions of steps a) and b) and dilution with water.

The invention also relates to a method for preparing an aqueous tank-mix comprising the steps of a) providing a composition containing the pyripyropene pesticide of the formulae I or II and the base and b') dilution of the composition obtained in step a) with water.

Furthermore, the invention relates to the use of the base for increasing the stability of the pyripyropene pesticide of the formulae I or II in agricultural compositions; and to a kit of parts comprising, as separate components, a) the pyripyropene of the formulae I or II, and b) the adjuvant, for combined use.

Further subject matters are a method for protecting plants from attack or infestation by insects, acarids or nematodes comprising contacting the plant, or the soil or water in which the plant is growing, with said composition in pesticidally effective amounts; a method for controlling insects, arachnids or nematodes comprising contacting an insect, acarid or nematode or their food supply, habitat, breeding grounds or their locus with said composition in pesticidally effective amounts; a method for protection of plant propagation material comprising contacting the plant propagation material, preferably seeds, with said composition in pesticidally effective amounts; and finally seed, comprising said composition.

The improvement of the insecticidal activity of pyripyropene A in agrochemical formulations is another aspect of the present invention. The development of a novel pest control composition comprising pyropyripene A as naturally derived insecticide itself having effective insectidal activity is desirable. Therefore it was another object of the present invention to find a way also to stabilze Insecticide B, and to increase, to improve and/or to prolong its storage time in agrochemical formulations.

The pesticide compound of the formulae I or II may be present in the composition in any form, such as dissolved, suspended, or emulsified. Preferably it is present in dissolved form.

Bases are typically compounds, which have a pH value of at least 7.0, preferably at least 7.5, in particular at least 8.0 in water at 20° C. at a concentration of 0.1 mol/l. In other words, bases are compounds an aqueous solution of which has a pH value of at least 7.0, preferably at least 7.5, in particular at least 8.0 in water at 20° C. at a concentration of 0.1 mol/l. Often, said pH value is in a range from 7.0 to 14.0, preferably from 7.5 to 12.0, and in particular from 8.0 to 10.0. Thus, the acidity constant $pK_a$ of the protonated base (i.e. the conjugate acid) at 20° C. in water is generally at least 7.0, preferably at least 8.0 in particular at least 8.5, e.g. from 7.0 to 14, in particular from 8.0 to 13.0 and especially from 8.5 to 12.0.

Preferably the base has boiling point at 1013 mbar of at least 40° C., preferably at least 80° C., especially at least 150° C.

The base has usually a solubility in water of at least 0.1 g/l at 20° C., preferably at least 1.0 g/l and in particular at least 10 g/l.

Chemical classes of bases are for example metal hydroxides, inorganic anydrobases, inorganic salts of weak acids, or in particular amines, including ammonia and organic amines.

Preferred examples for metal hydroxides are water-soluble metal hydroxides with a solubility in water of at least 1 g/l at 20° C. Examples are sodium, barium-, strontium-, or calcium-hydroxide, preferably sodium- and calcium hydroxide.

Suitable inorganic anhydrobases are inorganic compounds which react with water while forming hydroxide ions. Examples for anhydrobases are bariumoxide or calciumoxide.

Suitable inorganic salts of weak acids are carbonate and phosphate, such as potassium carbonate, sodium carbonate, trisodium phosphate.

Suitable amines are usually organic compounds comprising at least one primary, secondary, and/or tertiary amino group. Preferably the amines comprise at least one secondary and/or tertiary amino group. In particular, the amines comprise at least one tertiary amino group.

The amines have typically a pH value of at least 7.0 (preferably at least 7.5, in particular at least 8.0) in water at 20° C. at a concentration of 0.1 mol/l. In other words, bases are preferably selected from those amines an aqueous solution of which has a pH value of at least 7.0, preferably at least 7.5, in particular at least 8.0 in water at 20° C. at a concentration of 0.1 mol/l. Often, said pH value is in a range from 7.0 to 14.0, preferably from 7.5 to 12.0, and in particular from 8.0 to 10.0. Preferred amines are those, where the acidity constant $pK_a$ of the conjugate ammonium ion at 20° C. in water is generally at least 7.0, preferably at least 8.0 in particular at least 8.5, e.g. from 7.0 to 14, in particular from 8.0 to 13.0 and especially from 8.5 to 12.0.

Usually, the boiling point at 1013 mbar of the amine is at least 40° C., preferably at least 80° C., and in particular at least 150° C. Preferably, the amine is free of an aromatic group.

The amine has usually a solubility in water of at least 0.1 g/l at 20° C., preferably at least 1.0 g/l and in particular at least 10 g/l.

Examples of amines are ammonia ($NH_3$), 2-(2-Aminoethoxy)ethanol (DGA), Dimethylamine (DMA), N-Aminopropylmorpholine (APM), Tetraethylenepentamine (TEPA), Dipropylene Triamine, Diethylenetriamine (DETA), Tetra (2-hydroxypropyl)ethylenediamine (Quadrol®), Triethanolamine (TEA), Hexamethylenediamine, Jeffamine D-230, Triisopropanolamine (TIPA), Hexamethylenetetramine, Diethylethanolamine (DEEA), DMF-DMA, 2-(Diethylamino)ethylamine, 2-Phenylethylamine, 3-(2-Ethylhexoxy) propylamine, 3-Ethoxypropylamine, 3-Methoxypropylamine, Butylamine, Cyclohexylamine, Di-2-Ethylhexylamine (DEHA), Dibutylamine, Diethylamine (DEA), Diethylamine (DEA), Dipropylamine, Dipropylene Triamine, Ditridecylamine (DTD Amine), Hexylamine, Isopropylamine, Pentamethyldiethylenetriamine (PM-DETA), Methoxyisopropylamine, N,N-Bis-3-aminopropylmethylamine (BAPMA), N,N-Dimethylisopropylamine, N-Ethyldiisopropylamine, N-Octylamine, 3-(2-aminoethylamino)propylamine (N3-Amine), Propylamine, Tributylamine, Tridecylamine, Tripropylamine, Tris-(2-ethylhexyl)amine (TEHA), tert-Butylamine (t-BA), Diisopropanolamine (DIPA), N,N-Dimethylethanolamine, N,N-Dimethylisopropanolamine, N-Methylethanolamine (NMEA), N-Methyldiethanolamine (MDEA), 2,6-Xylidine, Dicykan, Benzylamine, Dimethylcyclohexylamine (DMCHA), N,N-Dimethylbenzylamine (DMBA), N-(2-hydroxyethyl)aniline, o-Toluidine, Ethyl-(2-hydroxyethyl)aniline, 1.2-Propylenediamine (1.2-PDA), 1,3-Diaminopropane (DAP), Dimethyldicykan (DMDC), 3-Amino-propyldiethyleneglycol (Mono-TTD), 4,7,10-Trioxatridecane-1,13-Diame (TTD), 4,9-Dioxadodecane, 1,12-diamine (DODA), Dimethylaminopropylamine (DMAPA), Ethylenediamine (EDA), Isophoronediamine, Triethylenediame (TEDA), Bis(2-Dimethylaminoethyl)ether (BD-MAEE), N-(2-Aminoethyl)ethanolamine (AEE), N-Ethylpiperazine, 2,2-Dimethyl-propane-1,3-diamine, Piperazine, Diethanolamine (DEA), N-Ethylethanolamine (EEA), Monoethanolamine (MEOA), N-(2-Aminoethyl)ethanolamine, Polyetheramine D 2000 (PEA D 2000), Polyetheramine D 400 (PEA D 2000), Polyetheramine T403, 1-Methyl Imidazole, 1-Vinylimidazole, 2-Ethyl Imidazole, 2-Methyl Imidazole, Imidazole, 1,2-Dimethyl Imidazole, Morphline, Pyrrolidine, Diisopropanol-p-toluidine (PIIPT), Isopropanolamine, 2,2'-Dimorpholinyldiethylether (DMDEE), N-EthylMorpholine (NEM), N-Methylmorpholine, Dimethylaminoethoxyethanol (DMEE), N,N'-Dimethylpiperazine, Trimethylaminoethylethanolamine (TMAEEA), S-Triazine, 1,8-Diazabicyclo-5,4,0-undecene-7, N-(3-Aminopropyl)imidazole, N-Butylethanolamine (BEA), 3-((2-Hydroxyethyl)amino)propanol, 3-Amino-1-Propanol, 3-Dimethylaminopropane-1-ol, Aminoethylethanolamine (AEEA), M-methylmorpholine oxide (NMMO), N-aminoethylpiperazine (AEP), Dimethylpiperazine (DMP), Methoxypropylamine (MOPA), Tetramethylbis (aminoethyl)ether(ZF-20), N,N-dimethyl-2(2-aminoethoxy) ethanol (ZR-70), Pentamethyldipropylenetriamine (ZR-40), Tetramethyldipropylenetriamine (Z-130), Benzyldimethylamine (BDMA), Triethylenetetramine (TETA), Jeffamine® D-400, Monoisopropanolamine (MIPA).

Further suitable amines are amines which comprise an alkoxylated amino group. Preferred are alkoxylated $C_{8-24}$ fatty amines, especially ethoxylated $C_{12-20}$ fatty amines. Examples are ethoxylated coco amine, POE 2 (Agnique® CAM-2), ethoxylated coco amine, POE 10 (Agnique® CAM-10), ethoxylated coco amine, POE 15 (Agnique® CAM-15), ethoxylated coco amine, POE 20 (Agnique® CAM-20), ethoxylated oleyl amine, POE 30 (Agnique® OAM-30), ethoxylated tallow amine, POE 5 (Agnique® TAM-5), ethoxylated tallow amine, POE 10 (Agnique® TAM-10), ethoxylated tallow amine, POE 15 (Agniqu® TAM-15), ethoxylated tallow amine, POE 20 (Agnique® TAM-20), ethoxylated tallow amine, POE 50 (Agnique® TAM-50), ethoxylated stearyl amine, POE 50 (Agnique® SAM-50). The Agnique product series is available from Cognis.

Suitable organic amines are in particular those of the formula III

where $R^1$ is H, $C_1$-$C_4$-alkyl, or a radical $(A-O)_nH$, in particular a radical of the formula $(A-O)_nH$, A is $C_2$-$C_4$-alkandiyl, in particular 1,2-ethandiyl or 1,2-propandiyl, m is an integer from 1 to 100, in particular 1 to 50, m may also be 0, if at least one of $R^1$, $R^2$ and in particular both $R^1$ and $R^2$ is/are different from H;

n is an integer from 1 to 100, in particular from 1 to 50, $R^2$ is H, $C_1$-$C_{30}$ alkyl, $C_2$-$C_{30}$ alkenyl or a radical of formula $-[A'-N(R^3)]_k-A'-NR^4R^5$, where A' is $C_2$-$C_4$-alkandiyl, in particular 1,2-ethandiyl, 1,2-propandiyl, 1,3-propandiyl or 1,4-butandiyl, k is an integer from 0 to 10, in particular 0, 1 or 2, $R^3$ is H, $C_1$-$C_4$-alkyl, or a radical $(A-O)_nH$, in particular a radical $(A-O)_nH$, $R^4$ is H, $C_1$-$C_4$-alkyl, or a radical $(A-O)_nH$, in particular a radical $(A-O)_nH$, and $R^5$ is H, $C_1$-$C_4$-alkyl, or a radical $(A-O)_nH$, in particular a radical $(A-O)_nH$, or $NR^4R^5$ represent an N-bound pyrrolidinyl, piperidinyl, piperazinyl or morpholinyl radical.

Here and in the following, the suffix $C_n$-$C_m$ indicates the number range for the number of possible carbon atoms of the respective radical. Hence, $C_1$-$C_{30}$ alkyl is a linear or branched alkyl radical having from 1 to 30 carbon atoms. Likewise, $C_2$-$C_{30}$ alkenyl is a linear or branched aliphatic radical having from 1 to 30 carbon atoms, which has at least 1, e.g. 1, 2 or 3 C=C-double bonds. $C_1$-$C_4$ Alkyl is a linear or branched alkyl radical having from 1 to 4 carbon atoms, examples including methyl, ethyl, n-propyl, isopropyl, n-butyl, 2-butyl, isobutyl (=2-methylpropan-1-yl) or tert.-butyl (=2-methylpropan-2-yl). $C_2$-$C_4$ Alkandiyl is a linear or branched divalent alkyl radical having from 2 to 4 carbon atoms, examples including 1,2-ethandiyl, 1,2-propandiyl, 1,3-propandiyl, 1,2-butandiyl, 1,3-butandiyl, 1,1-dimethylethan-1,2-diyl 1,2-dimethylethan-1,2-diyl or 1,4-butandiyl.

Amongst the amines of formula III those are preferred, where m is from 1 to 100, in particular from 1 to 50 and $R^1$ is a radical of the formula $(A-O)_nH$, where n is from 1 to 50 in particular from 1 to 50.

Amongst the amines of formula III those are preferred, where $R^2$ is $C_5$-$C_{30}$ alkyl, $C_5$-$C_{30}$ alkenyl or a radical of formula $-[A'-N(R^3)]_k-A'-N-NR^4R^5$, where A' is $C_2$-$C_4$-alkandiyl, in particular 1,2-ethandiyl, 1,2-propandiyl, 1,3-propandiyl or 1,4-butandiyl, k is an integer from 0 to 10, in particular 0, 1 or 2, $R^3$, $R^4$ and $R^5$, independently from each other are selected from the group consisting of is H, $C_1$-$C_4$-alkyl and a radical $(A-O)_nH$, in particular a radical $(A-O)_nH$, where A and n are as defined above and were n is in particular from 1 to 50 and where A is in particular 1,2-ethandiyl or 1,2-propandiyl.

Amongst the amines of formula III those are particularly preferred, where $R^2$ is $C_5$-$C_{30}$ alkyl or $C_5$-$C_{30}$ alkenyl, especially $C_8$-$C_{24}$ alkyl or $C_8$-$C_{24}$ alkenyl, m is from 1 to 50, in particular from 2 to 50 and $R^2$ is a radical of the formula $(A-O)_n H$, where A and n are as defined above and were n is in particular from 1 to 50, especially from 2 to 50 and where A is in particular 1,2-ethandiyl or 1,2-propandiyl.

Amongst the amines of formula III those are likewise preferred, where $R^2$ is radical of formula $[A'-N(R^3)]_k$-$A'$-$NR^4R^5$, where $A'$ is $C_2$-$C_4$-alkandiyl, in particular 1,2-ethandiyl, 1,2-propandiyl, 1,3-propandiyl or 1,4-butandiyl, k is as defined above, in particular 0, 1 or 2, $R^3$, $R^4$ and $R^5$, independently from each other are selected from the group consisting of is H, $C_1$-$C_4$-alkyl and a radical $(A-O)_n H$, in particular a radical $(A-O)_n H$, where A and n are as defined above and were n is in particular from 1 to 10 and where A is in particular 1,2-ethandiyl or 1,2-propandiyl, m is from 1 to 50, in particular from 1 to 10 and $R^2$ is a radical of the formula $(A-O)_n H$, where A and n are as defined above and were n is in particular from 1 to 10 and where A is in particular 1,2-ethandiyl or 1,2-propandiyl.

Particularly preferred bases are amines which contain at least one secondary and/or tertiary amino group, especially those amines which contain at least one tertiary amino group, and amines which comprise an alkoxylated amino group, in particular those of the formula III, preferably alkoxylated $C_{8-24}$ fatty amines, in particular those of the formula III, where $R^2$ is $C_8$-$C_{24}$ alkyl or $C_8$-$C_{24}$ alkenyl, in particular $C_{10}$-$C_{22}$ alkyl or $C_{10}$-$C_{22}$ alkenyl, m is from 1 to 50, in particular from 2 to 50 and $R^2$ is a radical of the formula $(A-O)_n H$, where A and n are as defined above and were n is in particular from 1 to 50, especially from 2 to 50 and where A is in particular 1,2-ethandiyl or 1,2-propandiyl. Examples such fatty amines include ethoxylated coco amine, POE 2 (Agnique® CAM-2), ethoxylated coco amine, POE 10 (Agnique® CAM-10), ethoxylated coco amine, POE 15 (Agnique® CAM-15), ethoxylated coco amine, POE 20 (Agnique® CAM-20), ethoxylated oleyl amine, POE 30 (Agnique® OAM-30), ethoxylated tallow amine, POE 5 (Agnique® TAM-5), ethoxylated tallow amine, POE 10 (Agnique® TAM-10), ethoxylated tallow amine, POE 15 (Agniqu® TAM-15), ethoxylated tallow amine, POE 20 (Agnique® TAM-20), ethoxylated tallow amine, POE 50 (Agnique® TAM-50), ethoxylated stearyl amine, POE 50 (Agnique® SAM-50).

The concentration of the base in the composition according to the invention is preferably selected from such an range which results in a pH of at least 6.0 after dilution of the composition to a concentration of 1.0 wt % in water (usually measured at 20° C.). In other words, the concentration of the base in the composition according to the invention is preferably chosen in such a manner that upon dilution of the composition in water to a concentration of 1.0 wt % (amount of formulation in water) a pH value of the aqueous dilution of at least 6.0, in particular at least 7.0, e.g. a pH in the range from 6.0 to 13.0, in particular 7.0 to 12.0 (measured at 20° C. will result. An expert may easily adjust the concentration accordingly, for example with the help of a standard pH-meter. In case he finds a pH which is below 6.0, he may simply increase the concentration of the base. In case he finds a pH which is too high, he may simply decrease the concentration of the base. Preferably the concentration of the base in the composition will be in the range from 0.1 to 10 wt %, in particular from 0.2 to 5 wt %, based on the weight of the composition.

The term wt %, as used herein, has to be understood as % by weight.

In a particular embodiment of the invention, the composition comprises at least one adjuvant, in particularly at least one alkoxylated aliphatic alcohol. If the compositions according to the invention comprise at least one adjuvant, the concentration of the adjuvant in the composition is usually at least 10 wt %, e.g. form 10 to 70 wt %, preferably at least 15 wt %, and in particular from 15 to 50 wt %, based on the composition.

Suitable adjuvants are all known materials of this class and are known to an expert, for example from Hazen, Weed Technology, 2000, 14, 773-784 "Adjuvants-terminology, classification and chemistry". Examples are wetter-spreader adjuvants, sticker adjuvants, humectants, or penetration agents. Further examples are surfactants (e.g. nonionic, anionic, cationic or ampoteric), wetting agents, spreading agents, sticking agents, humectants, penetration agents (e.g. paraffinic or vegetable-derived crop oil concentrates, phytobland oils, emulsifiable crop oil, vegetable oil concentrates, modified vegetable oil). The definitions and examples of the aforementioned terms are given in Hazen (2000).

In a particular embodiment of the invention, the composition in addition to the compound of formulae I or II and the base comprises at least one alkoxylated aliphatic alcohol, hereinafter also termed as alkoxylate. The aliphatic alcohol, on which the alkoxylated aliphatic alcohol is based, may be linear or branched. The aliphatic alcohol, on which the alkoxylated aliphatic alcohol is based, may have 5 to 36 carbon atoms, preferably it has 10 to 32 carbon atoms, more preferably 14 to 26 carbon atoms, and in particular 15 to 20 carbon atoms. It is also possible to use a mixture of alcoxylated aliphatic alcohols with different numbers of carbon atoms in the aliphatic radical of the aliphatic alcohol, on which the alkoxylated aliphatic alcohol is based. The aliphatic alcohol, on which the alkoxylated aliphatic alcohol is based, is preferably a linear aliphatic alcohol, and in particular a linear aliphatic alcohol with 14 to 22 carbon atoms or with 16 to 20 carbon atoms.

Alkoxylated in context with alkoxylated aliphatic alcohol means that the OH moiety of the aliphatic alcohol has been replaced by a polyoxyalkylene or polyalkyleneoxide moiety, which are synonyms. Polyoxyalkylene, in terms of the present invention, is an aliphatic polyether radical which build from alkylenoxide repeating units A-O, where A is alkandiyl, in particular $C_2$-$C_5$-alkandiyl. Polyoxyalkylene, in terms of the present invention, is preferably a poly-$C_2$-$C_5$-alkyleneoxide moiety, more preferably a poly-$C_2$-$C_4$-alkyleneoxide moiety, especially a poly-$C_2$-$C_3$-alkyleneoxide moiety, e.g. a polyethylenoxide moiety, a polypropylenoxide moiety, a poly(ethylenoxide-co-propylenoxide) moiety, a poly(ethylenoxide-co-butylenoxide) moiety or a poly(ethylenoxide-co-pentylenoxide) moiety. The number of alkyleneoxide repeating units in the polyoxyalkylene radical is generally from 1 to 100 or from 2 to 100, preferably from 5 to 40, more preferably from 10 to 30 and in particular from 12 to 20

In a particularly preferred embodiment the alkoxylated aliphatic alcohol (alkoxylate) is selected from alkoxylated alcohols of the formula (IV)

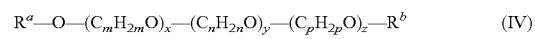  (IV)

in which
$R^a$ represents $C_5$-$C_{36}$-alkyl, $C_5$-$C_{36}$-alkenyl or mixture thereof, preferably linear $C_5$-$C_{36}$-alkyl, $C_5$-$C_{36}$-alkenyl, or a mixture thereof, in particular linear $C_{14}$-$C_{36}$-alkyl, $C_{14}$-$C_{36}$-alkenyl, or mixture thereof, or linear $C_{14}$-$C_{26}$-alkyl, $C_{14}$-$C_{26}$-alkenyl, or mixture thereof, more preferably linear $C_{14}$-$C_{22}$-alkyl, or mixture thereof, especially linear $C_{16}$-$C_{20}$-alkyl, or mixture thereof;

$R^b$ represents H or $C_1$-$C_{12}$-alkyl, in particular H or $C_1$-$C_4$-alkyl, preferably H or methyl, especially H;

m, n, p represent, independently of one another, an integer from 2 to 16, preferably from 2 to 5, more preferably 2, 3 or 2 and 3 (in particular 2 and 3);

x, y, z represent, independently of one another, a number from 0 to 100, preferably a number from 0 to 30, more preferably from 0 to 20; and x+y+z corresponds to a value from 1 to 100, preferably from 5 to 40, more preferably from 10 to 30 and in particular from 12 to 20.

$R^a$ may be linear or branched, preferably it is linear. $R^a$ may be saturated or unsaturated, preferably it is saturated. $R^a$ may be substituted or unsubstituted, preferably it is unsubstituted. Preferably, $R^a$ represents linear $C_5$-$C_{36}$-alkyl, $C_5$-$C_{36}$-alkenyl, or a mixture thereof. In particular, $R^a$ represents linear $C_{14}$-$C_{36}$-alkyl, $C_{14}$-$C_{36}$-alkenyl, or mixture thereof, in particular linear $C_{14}$-$C_{26}$-alkyl, $C_{14}$-$C_{26}$-alkenyl, or mixture thereof. More preferably, $R^a$ represents a linear $C_{14}$-$C_{22}$-alkyl, or mixture thereof. Especially preferred, $R^a$ represents a linear $C_{16}$-$C_{20}$-alkyl, or mixture thereof.

$R^b$ represents preferably H or methyl, in particular H.

Preferably, m, n, p represent, independently of one another, an integer from 2 to 5, more preferably 2, 3 or 2 and 3 (in particular 2 and 3).

Preferably, x, y, z represent, independently of one another, a number from 0 to 30, more preferably from 0 to 20. Preferably, x+y+z corresponds to a value from 5 to 40, more preferably from 10 to 30 and in particular from 12 to 20.

According to a special embodiment, alcohol alkoxylates of the formula (IV) are used in which m=2 and the value of x is greater than zero. This relates on this occasion to alcohol alkoxylates of EO type to which belong especially alcohol ethoxylates (m=2; x>zero; y, z=zero) and alcohol alkoxylates with an EO block bonded to the alcohol portion (m=2; x>zero; y and/or z>zero). Mention may be made, from the alcohol alkoxylates with an EO block bonded to the alcohol portion, especially of EO-PO block alkoxylates (m=2; x>zero; y>zero; n=3; z=0), EO-PeO block alkoxylates (m=2; x>zero; y>zero; n=5; z=0) and EO-PO-EO block alkoxylates (m, p=2; x, z>zero; y>zero; n=3). In particular preferred are EO-PO block alkoxylates (m=2; x>zero; y>zero; n=3; z=0).

Here and in the following EO represents $CH_2CH_2O$. PO represents $CH(CH_3)CH_2O$ or $CH_2CH(CH_3)O$. BuO represents $CH(C_2H_5)CH_2O$, $C(CH_3)_2CH_2O$, $CH_2C(CH_3)_2O$, $CH(CH_3)CH(CH_3)O$ or $CH_2CH(C_2H_5)O$ and PeO represents $(C_5H_{10}O)$.

Amongst the alkoxylated alcohols of formula (IV), preference is given to EO-PO block alkoxylates in which the ratio of EO to PO (x to y) is 10:1 to 1:10, preferably 1:1 to 1:12 and in particular 1:2 to 1:8. In this context, the degree of ethoxylation (value of x) is generally 1 to 20, preferably 2 to 15 and in particular 2 to 10 and the degree of propoxylation (value of y) is generally 1 to 30, preferably 4 to 20 and in particular 8 to 16. The overall degree of alkoxylation, i.e. the sum of EO and PO units, is generally 2 to 50, preferably 4 to 30 and in particular 6 to 20.

Amongst the alkoxylated alcohols of formula (IV), preference is furthermore given to EO-PeO block alkoxylates in which the ratio of EO to PeO (x to y) is 2:1 to 25:1 and in particular 4:1 to 15:1. In this context, the degree of ethoxylation (value of x) is generally 1 to 50, preferably 4 to 25 and in particular 6 to 15 and the degree of pentoxylation (value of y) is generally 0.5 to 20, preferably 0.5 to 4 and in particular 0.5 to 2. The overall degree of alkoxylation, i.e. the sum of EO and PeO units, is generally 1.5 to 70, preferably 4.5 to 29 and in particular 6.5 to 17.

According to a further particular embodiment, alcohol alkoxylates of the formula (IV) are used in which n=2, the values of x and y are both greater than zero and z=0. On this occasion also, these are alcohol alkoxylates of EO type but in which the EO block is terminally bonded. These include especially PO-EO block alkoxylates (n=2; x>zero; y>zero; m=3; z=0) and PeO-EO block alkoxylates (n=2; x>zero; y>zero; m=5; z=0).

Amongst the alkoxylated alcohols of formula (IV), preference is given to PO-EO block alkoxylates in which the ratio of PO to EO (x to y) is 1:10 to 10:1, preferably 12:1 to 1:1 and in particular 2:1 to 8:1. In this context, the degree of ethoxylation (value of y) is generally 1 to 20, preferably 2 to 15 and in particular 2 to 10. The degree of propoxylation (value of x) is generally 0.5 to 30, preferably 4 to 20 and in particular 6 to 16. The overall degree of alkoxylation, i.e. the sum of EO and PO units, is generally 1.5 to 50, preferably 2.5 to 30 and in particular 8 to 20.

Amongst the alkoxylated alcohols of formula (IV), preference is furthermore given to PeO-EO block alkoxylates in which the ratio of PeO to EO (x to y) is 1:50 to 1:3 and in particular 1:25 to 1:5. In this context, the degree of pentoxylation (value of x) is generally 0.5 to 20, preferably 0.5 to 4 and in particular 0.5 to 2 and the degree of ethoxylation (value of y) is generally 3 to 50, preferably 4 to 25 and in particular 5 to 15. The overall degree of alkoxylation, i.e. the sum of EO and PeO units, is generally 3.5 to 70, preferably 4.5 to 45 and in particular 5.5 to 17.

According to a further particular embodiment, alcohol alkoxylates of the formula (IV) are used in which the values of x, y and z are all greater than zero. These include especially PeO-EO-PO block alkoxylates (m=5; x>zero; n=2; y>zero; m=3; z>zero).

In an especially preferred embodiment the alkoxlyate is selected from alkoxylated alcohols of the formula (IV), in which $R^a$ represents linear $C_{12}$-$C_{22}$-alkyl, especially linear$C_{10}$-$C_{20}$ alkyl or a mixture thereof;

$R^b$ represents H or $C_1$-$C_4$-alkyl, preferably H or methyl, in particular H;

m, n, p represent, independently of one another, an integer from 2 to 5, preferably from 2 to 3;

x, y, z represent, independently of one another, a number from 0 to 50; and x+y+z corresponds to a value from 5 to 50, preferably from 8 to 25.

The wetting power by immersion of the alkoxlyate is usually at least 120 seconds, preferably at least 180 s, especially at least 220 s. The wetting power is usually analyzed according to DIN 1772 at room temperature at 1 g/L in 2 g/l sodium carbonate.

The surface tension of the alkoxylate is usually at least 30 mN/m, preferably at least 31 mN/m, and in particular at least 32 mN/m. Further on, the surface tension is preferably from 30 to 40 mN/m, and in particular from 30 to 35 mN/m. The surface tension may be analyzed according to DIN 14370 at room temperature at 1 g/L.

Preferably, the alkoxylate has a wetting power by immersion of at least 120 s and a surface tension of at least 30 mN/m. More preferably, the alkoxylate has a wetting power by immersion of at least 180 s and a surface tension from 30 to 40 mN/m.

Alkoxylates are known and may be prepared by known methods, such as WO 98/35553, WO 00/35278 or EP 0 681 865. Many alkoxlyates are commercially available, for example Atplus® 242, Atplus® 245, Atplus® MBA 1303 from Croda, Plurafac® LF types from BASF SE, Agnique® BP 24-24, Agnique® BP 24-36, Agnique® BP 24-45, Agnique® BP 24-54, Agnique® BP24-52R from Cognis.

The particularly preferred compositions according to the invention (most preferably in form of an emulsion concentrate) comprises usually at least 10 wt % of the alkoxylate, e.g. form 10 to 70 wt %, preferably at least 15 wt %, and in particular from 15 to 50 wt % based on the composition.

In the preferred composition according to the invention the alkoxylated aliphatic alcohol (alkoxylate) or the mixture of different alkoxylated alcohols may be the sole adjuvant. However, it is also preferred, if the alkoxylated aliphatic alcohol, in particular the alkoxylated aliphatic alcohol of formula (IV) is combined with a different adjuvant. In the preferred compositions according to the invention (preferably in form of an emulsion concentrate), which comprise at least one alkoxylated aliphatic alcohol and at least one adjuvant different therefrom, the total amount of adjuvant is generally at least 10 wt %, e.g. form 10 to 70 wt %, preferably at least 15 wt %, and in particular from 15 to 50 wt %, based on the composition.

The composition according to the present invention may be present in solid or liquid form, preferably in liquid form (such as aqueous or non-aqueous). Typically the composition is formulation as an agrochemical formulation. Examples of common formulation types are given below. In the composition the pesticide may be present in any form, such as dissolved, suspended, or emulsified. Preferably the pesticide compound of the formulae I or II is present in the composition in dissolved form or in suspended form. In particular, the composition the pesticide compound of the formulae I or II and the base is a liquid composition in the form of a solution or suspension or an emulsion, wherein the pesticide compound of the formulae I or II is present in dissolved form or in the form of suspended particles or in the form of emulsified droplets containing the pesticide compound in dissolved form.

The inventive composition may also comprise auxiliaries which are customary in agrochemical formulations. The auxiliaries used depend on the particular application form and active substance, respectively. Examples for suitable auxiliaries are solvents, solid carriers, dispersants or emulsifiers (such as further solubilizers, protective colloids, surfactants and adhesion agents), organic and inorganic thickeners, bactericides, anti-freezing agents, anti-foaming agents, if appropriate colorants and tackifiers or binders (e.g. for seed treatment formulations).

Suitable solvents are water, organic solvents such as mineral oil fractions of medium to high boiling point, such as kerosene or diesel oil, furthermore coal tar oils and oils of vegetable or animal origin, aliphatic, cyclic and aromatic hydrocarbons, e.g. toluene, xylene, paraffin, tetrahydronaphthalene, alkylated naphthalenes or their derivatives, alcohols such as methanol, ethanol, propanol, butanol and cyclohexanol, glycols, ketones such as cyclohexanone and gamma-butyrolactone, fatty acid dimethylamides, fatty acids and fatty acid esters and strongly polar solvents, e.g. amines such as N-methylpyrrolidone.

Solid carriers are mineral earths such as silicates, silica gels, talc, kaolins, limestone, lime, chalk, bole, loess, clays, dolomite, diatomaceous earth, calcium sulfate, magnesium sulfate, magnesium oxide, ground synthetic materials, fertilizers, such as, e.g., ammonium sulfate, ammonium phosphate, ammonium nitrate, ureas, and products of vegetable origin, such as cereal meal, tree bark meal, wood meal and nutshell meal, cellulose powders and other solid carriers.

Suitable surfactants (adjuvants, wetters, tackifiers, dispersants or emulsifiers) are alkali metal, alkaline earth metal and ammonium salts of aromatic sulfonic acids, such as ligninsoulfonic acid (Borrespense® types, Borregard, Norway) phenolsulfonic acid, naphthalenesulfonic acid (Morwet® types, Akzo Nobel, U.S.A.), dibutylnaphthalenesulfonic acid (Nekal® types, BASF, Germany), and fatty acids, alkylsulfonates, alkylarylsulfonates, alkyl sulfates, laurylether sulfates, fatty alcohol sulfates, and sulfated hexa-, hepta- and octadecanolates, sulfated fatty alcohol glycol ethers, furthermore condensates of naphthalene or of naphthalenesulfonic acid with phenol and formaldehyde, polyoxy-ethylene octylphenyl ether, ethoxylated isooctylphenol, octylphenol, nonylphenol, alkylphenyl polyglycol ethers, tributylphenyl polyglycol ether, tristearylphenyl polyglycol ether, alkylaryl polyether alcohols, alcohol and fatty alcohol/ethylene oxide condensates, ethoxylated castor oil, polyoxy-ethylene alkyl ethers, ethoxylated polyoxypropylene, lauryl alcohol polyglycol ether acetal, sorbitol esters, lignin-sulfite waste liquors and proteins, denatured proteins, polysaccharides (e.g. methylcellulose), hydrophobically modified starches, polyvinyl alcohols (Mowiol® types, Clariant, Switzerland), polycarboxylates (Sokolan® types, BASF, Germany), polyalkoxylates, polyvinylamines (Lupasol® types, BASF, Germany), polyvinylpyrrolidone and the copolymers therof.

Examples for thickeners (i.e. compounds that impart a modified flowability to formulations, i.e. high viscosity under static conditions and low viscosity during agitation) are polysaccharides and organic and anorganic clays such as Xanthan gum (Kelzan®, CP Kelco, U.S.A.), Rhodopol® 23 (Rhodia, France), Veegum® (R.T. Vanderbilt, U.S.A.) or Attaclay® (Engelhard Corp., NJ, USA). Bactericides may be added for preservation and stabilization of the formulation. Examples for suitable bactericides are those based on dichlorophene and benzylalcohol hemi formal (Proxel® from ICI or Acticide® RS from Thor Chemie and Kathon® MK from Rohm & Haas) and isothiazolinone derivatives such as alkylisothiazolinones and benzisothiazolinones (Acticide® MBS from Thor Chemie). Examples for suitable anti-freezing agents are ethylene glycol, propylene glycol, urea and glycerin. Examples for anti-foaming agents are silicone emulsions (such as e.g. Silikon® SRE, Wacker, Germany or Rhodorsil®, Rhodia, France), long chain alcohols, fatty acids, salts of fatty acids, fluoroorganic compounds and mixtures thereof. Suitable colorants are pigments of low water solubility and water-soluble dyes. Examples to be mentioned and the designations rhodamin B, C. I. pigment red 112, C. I. solvent red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108. Examples for tackifiers or binders are polyvinylpyrrolidons, polyvinylacetates, polyvinyl alcohols and cellulose ethers (Tylose®, Shin-Etsu, Japan).

Powders, materials for spreading and dusts can be prepared by mixing or concomitantly grinding the compounds the respective active compounds present in the inventive mixtures and, if appropriate, further active substances, with at least one solid carrier. Granules, e.g. coated granules, impregnated granules and homogeneous granules, can be prepared by binding the active substances to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, e.g., ammonium sulfate, ammonium phosphate, ammonium nitrate, ureas, and products of vegetable origin, such as cereal meal, tree bark meal, wood meal and nutshell meal, cellulose powders and other solid carriers.

Examples for agrochemical formulation types for the inventive composition are:

1. Composition Types for Dilution with Water i) Water-Soluble Concentrates (SL, LS)

10 parts by weight of active substance (e.g. Insecticide A) is dissolved in 90 parts by weight of water or in a water-soluble solvent. As an alternative, wetting agents or other auxiliaries are added. The active substance dissolves upon dilution with water. In this way, a formulation having a content of 10% by weight of active substance is obtained.

ii) Dispersible Concentrates (DC)

20 parts by weight of active substance (e.g. Insecticide A) is dissolved in 70 parts by weight of cyclohexanone with addition of 10 parts by weight of a dispersant, e.g. polyvinylpyrrolidone. Dilution with water gives a dispersion. The active substance content is 20% by weight.

iii) Emulsifiable Concentrates (EC)

15 parts by weight of active substance (e.g. Insecticide A) is dissolved in 75 parts by weight of xylene with addition of calcium dodecylbenzenesulfonate and castor oil ethoxylate (in each case 5 parts by weight). Dilution with water gives an emulsion. The composition has an active substance content of 15% by weight.

iv) Emulsions (EW, EO, ES)

25 parts by weight of active substance (e.g. Insecticide A) is dissolved in 35 parts by weight of xylene with addition of calcium dodecylbenzenesulfonate and castor oil ethoxylate (in each case 5 parts by weight). This mixture is introduced into 30 parts by weight of water by means of an emulsifying machine (Ultraturrax) and made into a homogeneous emulsion. Dilution with water gives an emulsion. The composition has an active substance content of 25% by weight.

v) Suspensions (SC, OD, FS)

In an agitated ball mill, 20 parts by weight of active substance (e.g. Insecticide A) is comminuted with addition of 10 parts by weight of dispersants and wetting agents and 70 parts by weight of water or an organic solvent to give a fine active substance suspension. Dilution with water gives a stable suspension of the active substance. The active substance content in the composition is 20% by weight.

vi) Water-Dispersible Granules and Water-Soluble Granules (WG, SG)

50 parts by weight of active substance (e.g. Insecticide A) is ground finely with addition of 50 parts by weight of dispersants and wetting agents and prepared as water-dispersible or water-soluble granules by means of technical appliances (e.g. extrusion, spray tower, fluidized bed). Dilution with water gives a stable dispersion or solution of the active substance. The composition has an active substance content of 50% by weight.

vii) Water-Dispersible Powders and Water-Soluble Powders (WP, SP, SS, WS)

75 parts by weight of active substance (e.g. Insecticide A) is ground in a rotor-stator mill with addition of 25 parts by weight of dispersants, wetting agents and silica gel. Dilution with water gives a stable dispersion or solution of the active substance. The active substance content of the composition is 75% by weight.

viii) Gel (GF)

In an agitated ball mill, 20 parts by weight active substance (e.g. Insecticide A) is comminuted with addition of 10 parts by weight of dispersants, 1 part by weight of a gelling agent wetters and 70 parts by weight of water or of an organic solvent to give a fine suspension of the active substance. Dilution with water gives a stable suspension of the active substance, whereby a composition with 20% (w/w) of active substance is obtained.

2. Composition Types to be Applied Undiluted ix) Dustable Powders (DP, DS)

5 parts by weight of active substance (e.g. Insecticide A) is ground finely and mixed intimately with 95 parts by weight of finely divided kaolin. This gives a dustable composition having an active substance content of 5% by weight.

x) Granules (GR, FG, GG, MG)

0.5 parts by weight of active substance (e.g. Insecticide A) is ground finely and associated with 99.5 parts by weight of carriers. Current methods are extrusion, spray-drying or the fluidized bed. This gives granules to be applied undiluted having an active substance content of 0.5% by weight.

xi) ULV Solutions (UL)

10 parts by weight of active substance (e.g. Insecticide A) is dissolved in 90 parts by weight of an organic solvent, e.g. xylene. This gives a composition to be applied undiluted having an active substance content of 10% by weight.

The agrochemical formulations generally comprise between 0.01 and 95%, preferably between 0.1 and 90%, most preferably between 0.5 and 90%, by weight of active substances. The Insecticide A is employed in a purity of from 90% to 100%, preferably from 95% to 100% (according to NMR spectrum).

The inventive composition can be used as such or in the form of their agrochemical formulations, e.g. in the form of directly sprayable solutions, powders, suspensions, dispersions, emulsions, oil dispersions, pastes, dustable products, materials for spreading, or granules, by means of spraying, atomizing, dusting, spreading, brushing, immersing or pouring. The application forms depend entirely on the intended purposes; it is intended to ensure in each case the finest possible distribution of the compounds present in the inventive compositions.

Aqueous application forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active substance concentrations in the ready-to-use preparations can be varied within relatively wide ranges. In general, they are from 0.0001 to 10%, preferably from 0.001 to 1% by weight of compounds of the inventive compositions.

The compounds of the inventive compositions may also be used successfully in the ultra-low-volume process (ULV), it being possible to apply compositions comprising over 95% by weight of active substance, or even to apply the active substance without additives.

Various types of oils, wetters, adjuvants, herbicides, fungicides, other pesticides, or bactericides may be added to the active compounds, if appropriate not until immediately prior to use (tank mix). These agents can be admixed with the compounds of the inventive composition in a weight ratio of 1:100 to 100:1, preferably 1:10 to 10:1.

Compositions of this invention may also contain fertilizers such as ammonium nitrate, urea, potash, and superphosphate, phytotoxicants and plant growth regulators and safeners. These may be used sequentially or in combination with the above-described compositions, if appropriate also added only immediately prior to use (tank mix). For example, the plant(s) may be sprayed with a composition of this invention either before or after being treated with the fertilizers.

The compounds of the inventive composition can be used individually or already partially or completely mixed with one another to prepare the composition according to the invention. It is also possible for them to be packaged and used further as combination composition such as a kit of parts. In one embodiment of the invention, a kit of parts comprises, as separate components, a) the pesticide, and b) the base, for combined use. The kits may include one or more, including all, components that may be used to prepare a subject agrochemical composition. In those embodiments where more than two components are provided in a kit, the components may already be combined together and as such are packaged in a single container such as a vial, bottle, can, pouch, bag or canister. In other embodiments, two or more components of a kit may be packaged separately, i.e., not pre-formulated. As such, kits may include one or more separate containers such as vials, cans, bottles, pouches, bags or canisters, each container containing a separate component for an agrochemical composition. In both forms, a component of the kit may be applied separately from or together with the further components or as a component of a combination composition according to the invention for preparing the composition according to the invention.

The user applies the composition according to the invention usually from a predosage device, a knapsack sprayer, a spray tank or a spray plane. Here, the agrochemical composition is made up with water and/or buffer to the desired application concentration, it being possible, if appropriate, to add further auxiliaries, and the ready-to-use spray liquor or the agrochemical composition according to the invention is thus obtained. Usually, 50 to 500 liters of the ready-to-use spray liquor are applied per hectare of agricultural useful area, preferably 100 to 400 liters.

The present invention further relates to a method for protecting plants from attack or infestation by insects, acarids or nematodes comprising contacting the plant, or the soil or water in which the plant is growing, with the inventive composition in pesticidally effective amounts.

The present invention further relates to a method for controlling insects, arachnids or nematodes comprising contacting an insect, acarid or nematode or their food supply, habitat, breeding grounds or their locus with the inventive composition in pesticidally effective amounts.

The inventive composition exhibits outstanding action against animal pests (e.g. insects, acarids or nematodes) from the following orders:

insects from the order of the lepidopterans (Lepidoptera), for example *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis*, beetles (Coleoptera), for example *Agrilus sinuatus, Agriotes lineatus, Agriotes obscurus, Amphimallus solstitialis, Anisandrus dispar, Anthonomus grandis, Anthonomus pomorum, Aphthona euphoridae, Athous haemorrhoidalis, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Cetonia aurata, Ceuthorrhynchus assimilis, Ceuthorrhynchus napi, Chaetocnema tibialis, Conoderus vespertinus, Crioceris asparagi, Ctenicera ssp., Diabrotica longicornis, Diabrotica semipunctata, Diabrotica 12-punctata Diabrotica speciosa, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllobius pyri, Phyllotreta chrysocephala, Phyllophaga sp., Phyllopertha horticola, Phyllotreta nemorum, Phyllotreta striolata, Popillia japonica, Sitona lineatus* and *Sitophilus granaria*, flies, mosquitoes (Diptera), e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Ceratitis capitata, Chrysomya bezziana, Chrysomya hominivorax, Chrysomya macellaria, Chrysops discalis, Chrysops silacea, Chrysops atlanticus, Cochliomyia hominivorax, Contarinia sorghicola Cordylobia anthropophaga, Culicoides furens, Culex pipiens, Culex nigripalpus, Culex quinquefasciatus, Culex tarsalis, Culiseta inornata, Culiseta melanura, Dacus cucurbitae, Dacus oleae, Dasineura brassicae, Delia antique, Delia coarctata, Delia platura, Delia radicum, Dermatobia hominis, Fannia canicularis, Geomyza Tripunctata, Gasterophilus intestinalis, Glossina morsitans, Glossina palpalis, Glossina fuscipes, Glossina tachinoides, Haematobia irritans, Haplodiplosis equestris, Hippelates* spp., *Hylemyia platura, Hypoderma lineata, Leptoconops torrens, Liriomyza sativae, Liriomyza trifolii, Lucilia caprina, Lucilia cuprina, Lucilia sericata, Lycoria pectoralis, Mansonia titillanus, Mayetiola destructor, Musca domestica, Muscina stabulans, Oestrus ovis, Opomyza florum, Oscinella frit, Pegomya hysocyami, Phorbia antiqua, Phorbia brassicae, Phorbia* coarctata, Phlebotomus argentipes, Psorophora columbiae, Psila rosae, Psorophora discolor, Prosimulium mixtum, Rhagoletis cerasi, Rhagoletis pomonella, Sarcophaga haemorrhoidalis, Sarcophaga sp., Simulium vittatum, Stomoxys calcitrans, Tabanus bovinus, Tabanus atratus, Tabanus lineola, and Tabanus similis, Tipula oleracea, and Tipula paludosa thrips (Thysanoptera), e.g. Dichromothrips corbetti, Dichromothrips ssp, Frankliniella fusca, Frankliniella occidentalis, Frankliniella tritici, Scirtothrips citri, Thrips oryzae, Thrips palmi and Thrips tabaci, termites (Isoptera), e.g. Calotermes flavicollis, Leucotermes flavipes, Heterotermes aureus, Reticulitermes flavipes, Reticulitermes virginicus, Reticulitermes lucifugus, Termes natalensis, and Coptotermes formosanus, cockroaches (Blattaria—Blattodea), e.g. Blattella germanica, Blattella asahinae, Periplaneta americana, Periplaneta japonica, Periplaneta brunnea, Periplaneta fuligginosa, Periplaneta australasiae, and Blatta orientalis, true bugs (Hemiptera), e.g. Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis, Thyanta perditor, Acyrthosiphon onobrychis, Adelges laricis, Aphidula nasturtii, Aphis fabae, Aphis forbesi, Aphis pomi, Aphis gossypii, Aphis grossulariae, Aphis schneideri, Aphis spiraecola, Aphis sambuci, Acyrthosiphon pisum, Aulacorthum solani, Bemisia argentifolii, Brachycaudus cardui, Brachycaudus helichrysi, Brachycaudus persicae, Brachycaudus prunicola, Brevicoryne brassicae, Capitophorus horni, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzus persicae, Myzus ascalonicus, Myzus cerasi, Myzus varians, Nasonovia ribis-nigri, Nilaparvata lugens, Pemphigus bursarius, Perkinsiella saccharicida, Phorodon humuli, Psylla mali, Psylla piri, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Trialeurodes vaporariorum, Toxoptera aurantiiand, Viteus vitifolii, Cimex lectularius, Cimex hemipterus, Reduvius senilis, Triatoma spp., and Arilus critatus.

ants, bees, wasps, sawflies (Hymenoptera), e.g. Athalia rosae, Atta cephalotes, Atta capiguara, Atta cephalotes, Atta laevigata, Atta robusta, Atta sexdens, Atta texana, Crematogaster spp., Hoplocampa minuta, Hoplocampa testudinea, Monomorium pharaonis, Solenopsis geminata, Solenopsis invicta, Solenopsis richteri, Solenopsis xyloni, Pogonomyrmex barbatus, Pogonomyrmex californicus, Pheidole megacephala, Dasymutilla occidentalis, Bombus spp. Vespula squamosa, Paravespula vulgaris, Paravespula pennsylvanica, Paravespula germanica, Dolichovespula maculata, Vespa crabro, Polistes rubiginosa, Camponotus floridanus, and Linepithema humile, crickets, grasshoppers, locusts (Orthoptera), e.g. Acheta domestica, Gryllotalpa gryllotalpa, Locusta migratoria, Melanoplus bivittatus, Melanoplus femurrubrum, Melanoplus mexicanus, Melanoplus sanguinipes, Melanoplus spretus, Nomadacris septemfasciata, Schistocerca americana, Schistocerca gregaria, Dociostaurus maroccanus, Tachycines asynamorus, Oedaleus senegalensis, Zonozerus variegatus, Hieroglyphus daganensis, Kraussaria angulifera, Calliptamus italicus, Chortoicetes terminifera, and Locustana pardalina, Arachnoidea, such as arachnids (Acarina), e.g. of the families Argasidae, Ixodidae and Sarcoptidae, such as Amblyomma americanum, Amblyomma variegatum, Ambryomma maculatum, Argas persicus, Boophilus annulatus, Boophilus decoloratus, Boophilus microplus, Dermacentor silvarum, Dermacentor andersoni, Dermacentor variabilis, Hyalomma truncatum, Ixodes ricinus, Ixodes rubicundus, Ixodes scapularis, Ixodes holocyclus, Ixodes pacificus, Ornithodorus moubata, Ornithodorus hermsi, Ornithodorus turicata, Ornithonyssus bacoti, Otobius megnini, Dermanyssus gallinae, Psoroptes ovis, Rhipicephalus sanguineus, Rhipicephalus appendiculatus, Rhipicephalus everti, Sarcoptes scabiei, and Eriophyidae spp. such as Aculus schlechtendali, Phyllocoptrata oleivora and Eriophyes sheldoni; Tarsonemidae spp. such as Phytonemus pallidus and Polyphagotarsonemus latus; Tenuipalpidae spp. such as Brevipalpus phoenicis; Tetranychidae spp. such as Tetranychus cinnabarinus, Tetranychus kanzawai, Tetranychus pacificus, Tetranychus telarius and Tetranychus urticae, Panonychus ulmi, Panonychus citri, and Oligonychus pratensis; Araneida, e.g. Latrodectus mactans, and Loxosceles reclusa, fleas (Siphonaptera), e.g. Ctenocephalides felis, Ctenocephalides canis, Xenopsylla cheopis, Pulex irritans, Tunga penetrans, and Nosopsyllus fasciatus, silverfish, firebrat (Thysanura), e.g. Lepisma saccharina and Thermobia domestica, centipedes (Chilopoda), e.g. Scutigera coleoptrata, millipedes (Diplopoda), e.g. Narceus spp., Earwigs (Dermaptera), e.g. forficula auricularia, lice (Phthiraptera), e.g. Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus and Solenopotes capillatus, plant parasitic nematodes such as root-knot nematodes, Meloidogyne arenaria, Meloidogyne chitwoodi, Meloidogyne exigua, Meloidogyne hapla, Meloidogyne incognita, Meloidogyne javanica and other Meloidogyne species; cyst nematodes, Globodera rostochiensis, Globodera pallida, Globodera tabacum and other Globodera species, Heterodera avenae, Heterodera glycines, Heterodera schachtii, Heterodera trifolii, and other Heterodera species; seed gall nematodes, Anguina funesta, Anguina tritici and other Anguina species; stem and foliar nematodes, Aphelenchoides besseyi, Aphelenchoides fragariae, Aphelenchoides ritzemabosi and other Aphelenchoides species; sting nematodes, Belonolaimus longicaudatus and other Belonolaimus species; pine nematodes, Bursaphelenchus xylophilus and other Bursaphelenchus species; ring nematodes, Criconema species, Criconemella species, Criconemoides species, and Mesocriconema species; stem and bulb nematodes, Ditylenchus destructor, Ditylenchus dipsaci, Ditylenchus myceliophagus and other Ditylenchus species; awl nematodes, Dolichodorus species; spiral nematodes, Helicotylenchus dihystera, Helicotylenchus multicinctus and other Helicotylenchus species, Rotylenchus robustus and other Rotylenchus species; sheath nematodes, Hemicycliophora species and Hemicriconemoides species; Hirshmanniella species; lance nematodes, Hoplolaimus columbus, Hoplolaimus galeatus and other Hoplolaimus species; false root-knot nematodes, Nacobbus aberrans and other Nacobbus species; needle nematodes, Longidorus elongates and other Longidorus species; pin nematodes, Paratylenchus species; lesion nematodes, Pratylenchus

*brachyurus*, *Pratylenchus coffeae*, *Pratylenchus curvitatus*, *Pratylenchus goodeyi*, *Pratylencus neglectus*, *Pratylenchus penetrans*, *Pratylenchus scribneri*, *Pratylenchus vulnus*, *Pratylenchus zeae* and other *Pratylenchus* species; *Radinaphelenchus cocophilus* and other *Radinaphelenchus* species; burrowing nematodes, *Radopholus similis* and other *Radopholus* species; reniform nematodes, *Rotylenchulus reniformis* and other *Rotylenchulus* species; *Scutellonema* species; stubby root nematodes, *Trichodorus primitivus* and other *Trichodorus* species; *Paratrichodorus minor* and other *Paratrichodorus* species; stunt nematodes, *Tylenchorhynchus claytoni*, *Tylenchorhynchus dubius* and other *Tylenchorhynchus* species and *Merlinius* species; citrus nematodes, *Tylenchulus semipenetrans* and other *Tylenchulus* species; dagger nematodes, *Xiphinema americanum*, *Xiphinema index*, *Xiphinema diversicaudatum* and other *Xiphinema* species; and other plant parasitic nematode species.

The composition according to the invention can be applied to any and all developmental stages of pests, such as egg, larva, pupa, and adult. The pests may be controlled by contacting the target pest, its food supply, habitat, breeding ground or its locus with a pesticidally effective amount of the inventive compositions. "Locus" means a plant, plant propagation material (preferably seed), soil, area, material or environment in which a pest is growing or may grow.

In general, "pesticidally effective amount" means the amount of the inventive compositions needed to achieve an observable effect on growth, including the effects of necrosis, death, retardation, prevention, and removal, destruction, or otherwise diminishing the occurrence and activity of the animal pest. The pesticidally effective amount can vary for the various compositions used in the invention. A pesticidally effective amount of the compositions will also vary according to the prevailing conditions such as desired pesticidal effect and duration, weather, target species, locus, mode of application, and the like.

The inventive compositions are employed by treating the animal pest or the plants, plant propagation materials (preferably seeds), materials or soil to be protected from pesticidal attack with a pesticidally effective amount of the active compounds. The application can be carried out both before and after the infection of the materials, plants or plant propagation materials (preferably seeds) by the pests.

Preferably, the inventive compositions are employed by treating the animal pests or the plants or soil to be protected from pesticidal attack via foliar application with a pesticidally effective amount of the active compounds. Also herein, the application can be carried out both before and after the infection of the plants by the pests.

In the method of combating animal pests (insects, acarids or nematodes) depending on the type of compound and the desired effect, the application rates of the compositions according to the invention are from 0.1 g/ha to 10000 g/ha, preferably 1 g/ha to 5000 g/ha, more preferably from 20 to 1000 g/ha, most preferably from 10 to 750 g/ha, in particular from 20 to 500 g/ha.

In the context of the present invention, the term plant refers to an entire plant, a part of the plant or the propagation material of the plant.

Plants and as well as the propagation material of said plants, which can be treated with the inventive compositions include all genetically modified plants or transgenic plants, e.g. crops which tolerate the action of herbicides or fungicides or insecticides owing to breeding, including genetic engineering methods, or plants which have modified characteristics in comparison with existing plants, which can be generated for example by traditional breeding methods and/or the generation of mutants, or by recombinant procedures.

For example, compositions according to the present invention can be applied (as seed treatment, spray treatment, in furrow or by any other means) also to plants which have been modified by breeding, mutagenesis or genetic engineering including but not limiting to agricultural biotech products on the market or in development. Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-transitional modification of protein(s), oligo- or poly-peptides e.g. by glycosylation or polymer additions such as prenylated, acetylated or farnesylated moieties or PEG moieties.

Plants that have been modified by breeding, mutagenesis or genetic engineering, e.g. have been rendered tolerant to applications of specific classes of herbicides, such as hydroxyphenylpyruvate dioxygenase (HPPD) inhibitors; acetolactate synthase (ALS) inhibitors, such as sulfonyl ureas (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073) or imidazolinones (see e.g. U.S. Pat. No. 6,222,100, WO 01/82685, WO 00/026390, WO 97/41218, WO 98/002526, WO 98/02527, WO 04/106529, WO 05/20673, WO 03/014357, WO 03/13225, WO 03/14356, WO 04/16073); enolpyruvylshikimate-3-phosphate synthase (EPSPS) inhibitors, such as glyphosate (see e.g. WO 92/00377); glutamine synthetase (GS) inhibitors, such as glufosinate (see e.g. EP-A 242 236, EP-A 242 246) or oxynil herbicides (see e.g. U.S. Pat. No. 5,559,024) as a result of conventional methods of breeding or genetic engineering. Several cultivated plants have been rendered tolerant to herbicides by conventional methods of breeding (mutagenesis), e.g. Clearfield® summer rape (Canola, BASF SE, Germany) being tolerant to imidazolinones, e.g. imazamox. Genetic engineering methods have been used to render cultivated plants such as soybean, cotton, corn, beets and rape, tolerant to herbicides such as glyphosate and glufosinate, some of which are commercially available under the trade names RoundupReady® (glyphosate-tolerant, Monsanto, U.S.A.) and LibertyLink® (glufosinate-tolerant, Bayer CropScience, Germany).

Furthermore, plants are also covered that are by the use of recombinant DNA techniques capable to synthesize one or more insecticidal proteins, especially those known from the bacterial genus Bacillus, particularly from *Bacillus thuringiensis*, such as δ-endotoxins, e.g. CryIA(b), CryIA(c), CryIF, CryIF(a2), CryIIA(b), CryIIIA, CryIIIB(b1) or Cry9c; vegetative insecticidal proteins (VIP), e.g. VIP1, VIP2, VIP3 or VIP3A; insecticidal proteins of bacteria colonizing nematodes, e.g. *Photorhabdus* spp. or *Xenorhabdus* spp.; toxins produced by animals, such as scorpion toxins, arachnid toxins, wasp toxins, or other insect-specific neurotoxins; toxins produced by fungi, such *Streptomycetes* toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e.g. WO 02/015701). Further examples of such toxins or genetically modified plants capable of synthesizing such toxins are disclosed, e.g., in EP-A 374 753, WO 93/007278, WO 95/34656, EP-A 427 529, EP-A 451 878, WO 03/18810 and WO 03/52073. The methods for producing such genetically modified plants are generally known to the person skilled in the art and are described, e.g. in the publications mentioned above. These insecticidal proteins contained in the genetically modified plants impart to the plants producing these proteins tolerance to harmful pests from all taxonomic groups of athropods, especially to beetles (Coeloptera), two-winged insects (Diptera), and moths (Lepidoptera) and to nematodes (Nematoda). Genetically modified plants capable to synthesize one or more insecticidal proteins are, e.g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e.g. Agrisure® CB) and Bt176 from Syngenta Seeds SAS, France, (corn cultivars producing the Cry1Ab toxin and PAT enyzme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e.g. EP-A 392 225), plant disease resistance genes (e.g. potato cultivars, which express resistance genes acting against *Phytophthora infestans* derived from the mexican wild potato *Solanum bulbocastanum*) or T4-lysozym (e.g. potato cultivars capable of synthesizing these proteins with increased resistance against bacteria such as *Erwinia amylvora*). The methods for producing such genetically modified plants are generally known to the person skilled in the art and are described, e.g. in the publications mentioned above.

Furthermore, plants are also covered that are by the use of recombinant DNA techniques capable to synthesize one or more proteins to increase the productivity (e.g. bio mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of substances of content or new substances of content, specifically to improve human or animal nutrition, e.g. oil crops that produce health-promoting long-chain omega-3 fatty acids or unsaturated omega-9 fatty acids (e.g. Nexera® rape, DOW Agro Sciences, Canada).

Furthermore, plants are also covered that contain by the use of recombinant DNA techniques a modified amount of substances of content or new substances of content, specifically to improve raw material production, e.g. potatoes that produce increased amounts of amylopectin (e.g. Amflora® potato, BASF SE, Germany).

The inventive composition are effective through both contact (via soil, glass, wall, bed net, carpet, plant parts or animal parts), and ingestion (bait, or plant part) and through trophallaxis and transfer.

Preferred application methods are into water bodies, via soil, cracks and crevices, pastures, manure piles, sewers, into water, on floor, wall, or by perimeter spray application and bait.

According to another preferred embodiment of the invention, for use against non phytophathogenic pests such as ants, termites, wasps, flies, mosquitoes, crickets, locusts, or cockroaches the inventive composition are prepared into a bait preparation.

The bait can be a liquid, a solid or a semisolid preparation (e.g. a gel). The bait employed in the composition is a product which is sufficiently attractive to incite insects such as ants, termites, wasps, flies, mosquitoes, crickets etc. or cockroaches to eat it. This attractant may be chosen from feeding stimulants or para and/or sex pheromones readily known in the art.

Methods to control infectious diseases transmitted by non-phytophathogenic insects (e.g. malaria, dengue and yellow fever, lymphatic filariasis, and leishmaniasis) with the inventive compositions and their respective compositions also comprise treating surfaces of huts and houses, air spraying and impregnation of curtains, tents, clothing items, bed nets, tsetse-fly trap or the like. Insecticidal compositions for application to fibers, fabric, knitgoods, non-wovens, netting material or foils and tarpaulins preferably comprise a composition including the inventive compositions, optionally a repellent and at least one binder.

The inventive compositions can be used for protecting wooden materials such as trees, board fences, sleepers, etc. and buildings such as houses, outhouses, factories, but also construction materials, furniture, leathers, fibers, vinyl articles, electric wires and cables etc. from ants and/or termites, and for controlling ants and termites from doing harm to crops or human being (e.g. when the pests invade into houses and public facilities).

In the case of soil treatment or of application to the pests dwelling place or nest, the quantity of active ingredient ranges from 0.0001 to 500 g per 100 m$^2$, preferably from 0.001 to 20 g per 100 m$^2$.

Customary application rates in the protection of materials are, for example, from 0.01 g to 1000 g of active compound per m$^2$ treated material, desirably from 0.1 g to 50 g per m$^2$.

Insecticidal compositions for use in the impregnation of materials typically contain from 0.001 to 95 weight %, preferably from 0.1 to 45 weight %, and more preferably from 1 to 25 weight % of at least one repellent and/or insecticide.

For use in bait compositions, the typical content of active ingredient is from 0.0001 weight % to 15 weight %, desirably from 0.001 weight % to 5% weight % of active compound. The composition used may also comprise other additives such as a solvent of the active material, a flavoring agent, a preserving agent, a dye or a bitter agent. Its attractiveness may also be enhanced by a special color, shape or texture.

For use in spray compositions, the content of the composition of the active ingredients is from 0.001 to 80 weights %, preferably from 0.01 to 50 weight % and most preferably from 0.01 to 15 weight %.

The invention further relates to a method for protection of plant propagation material comprising contacting the plant propagation material with a composition according to the invention in pesticidally effective amounts.

As mentioned at the outset, in a preferred embodiment of the invention, the inventive compositions are used for the protection of the seed and the seedlings' roots and shoots, preferably the seeds.

Seed treatment can be made into the seedbox before planting into the field.

For seed treatment purposes, the weight ration in the inventive composition generally depends from the properties of the compounds of the inventive compositions.

Customary formulations, which are especially useful for seed treatment are e.g.:

A Soluble concentrates (SL, LS)
D Emulsions (EW, EO, ES)
E Suspensions (SC, OD, FS)
F Water-dispersible granules and water-soluble granules (WG, SG)
G Water-dispersible powders and water-soluble powders (WP, SP, WS)
H Gel-Formulations (GF)
I Dustable powders (DP, DS)

These compositions can be applied to plant propagation materials, particularly seeds, diluted or undiluted. These compositions can be applied to plant propagation materials, particularly seeds, diluted or undiluted. The compositions in question give, after two-to-tenfold dilution, active substance concentrations of from 0.01 to 60% by weight, preferably from 0.1 to 40% by weight, in the ready-to-use preparations. Application can be carried out before or during sowing.

Methods for applying the inventive composition and compositions thereof, respectively, on to plant propagation material, especially seeds, are known in the art, and include but not limited to, seed dressing, seed coating, seed dusting, seed soaking, seed film coating, seed multilayer coating, seed encrusting, seed dripping, and seed pelleting.

In a preferred embodiment, the compounds or the compositions thereof, respectively, are applied on to the plant propagation material by a method such that germination is not induced, e.g. by seed dressing, pelleting, coating and dusting.

In the treatment of plant propagation material (preferably seed), the application rates of the inventive composition are generally for the formulated product (which usually comprises from 10 to 750 g/l of the active(s)).

The invention also relates to the propagation products of plants, and especially the seed comprising, that is, coated with and/or containing, an inventive composition as defined above. The plant propagation material (preferably seed) comprises the inventive compositions in an amount of from 0.1 g to 10 kg per 100 kg of plant propagation material (preferably seed), preferably 0.1 g to 1 kg per 100 kg of plant propagation material (preferably seed).

The separate or joint application of the compounds of the inventive compositions is carried out by spraying or dusting the seeds, the seedlings, the plants or the soils before or after sowing of the plants or before or after emergence of the plants.

In accordance with one variant of soil application, a further subject of the invention is in furrow treatment, which comprises adding a solid or liquid formulation comprising the inventive compositions to the open furrow, in which seeds have been sown or, alternatively, applying seeds and formulation simultaneously to the open furrow.

In an especially preferred embodiment, the composition according to the invention is an emulsion concentrate (EC), which comprises the base, in particular an amine, especially an amine of formula III. Preferably the EC comprises 0.5 to 30 wt %, in particular 1 to 15 wt % of Insecticide A, the base, and formulation auxiliaries up to 100%, where the formulation auxiliaries usually comprise from 10 to 70% by weight, in particular form 25 to 60 wt % of at least one organic solvent, wherein all components sum up to 100 wt %, i.e. the wt % values are based on the total weight of the composition. The concentration of the base in these EC's is selected from such an range which results of a pH of at least 6.0, in particular a pH of at least 6.5, especially a pH of at least 7.0, e.g. a pH of from 6.0 to 13, in particular from 6.5 to 12 especially from 7.0 to 10, after dilution to 1.0 wt % with water. Preferably the concentration of the base in the emulsion concentrate is from 0.1 to 10 wt %, in particular from 0.2 to 5.0 wt %, based on the composition.

Likewise, preferably the EC comprises 0.5 to 30 wt %, in particular 1 to 15 wt % of Insecticide B, the base, and formulation auxiliaries up to 100%, where the formulation auxiliaries usually comprise from 10 to 70% by weight, in particular form 25 to 60 wt % of at least one organic solvent, wherein all components sum up to 100 wt %, i.e. the wt % values are based on the total weight of the composition. The concentration of the base in these EC's is selected from such an range which results of a pH of at least 6.0, in particular a pH of at least 6.5, especially a pH of at least 7.0, e.g. a pH of from 6.0 to 13, in particular from 6.5 to 12 especially from 7.0 to 10, after dilution to 1.0 wt % with water. Preferably the concentration of the base in the emulsion concentrate is from 0.1 to 10 wt %, in particular from 0.2 to 5.0 wt %, based on the composition.

In particular, the EC comprises 1 to 15 wt % of Insecticide A or of Insecticide B, the base, in particular an amine, especially an amine of formula III, 25 to 60 wt % of organic solvent, and formulation auxiliaries up to 100 wt %, wherein all components sum up to 100 wt %, i.e. the wt % values are based on the total weight of the composition. The concentration of the base in the EC is selected from such an range which results of a pH of at least 6.5, in particular a pH of at least 7.0, e.g. a pH of from 6.0 to 13, in particular from 6.5 to 12 especially from 7.0 to 10, after dilution to 1.0 wt % with water.

Preferably the concentration of the base in the emulsion concentrate is from 0.1 to 10 wt %, in particular from 0.2 to 5.0 wt %, based on the composition.

In an especially preferred embodiment, the composition according to the invention is an emulsion concentrate (EC), which comprises the base, in particular an amine, especially an amine of formula III and an adjuvant, in particular an alkoxylated aliphatic alcohol, especially an alcohol of formula (IV). Preferably the EC comprises 0.5 to 30 wt %, in particular from 1 to 15 wt % of Insecticide A or of Insecticide B, the base, the adjuvant and formulation auxiliaries up to 100%, where the formulation auxiliaries usually comprise from 10 to 70% by weight, in particular form 25 to 60 wt % of at least one organic solvent, wherein all components sum up to 100 wt %, i.e. the wt % values are based on the total weight of the composition. Preferably the concentration of the base in said EC is from 0.1 to 10 wt %, in particular from 0.2 to 5.0 wt %, based on the total weight of the composition. Preferably, the amount of adjuvant in said emulsion concentrate is from 10 to 70% by weight, in particular from 15 to 50 wt %, based on the total weight of the composition.

In particular, the EC comprises 1 to 15 wt % Insecticide A or of Insecticide B, the base, in particular an amine, especially an amine of formula III, 25 to 60 wt % organic solvent, and formulation auxiliaries up to 100 wt %, wherein all components sum up to 100 wt %, i.e. the wt % values are based on the total weight of the composition. Preferably the concentration of the base in the EC is from 0.1 to 10 wt %, in particular from 0.2 to 5.0 wt %, based on the composition. Preferably, the amount of adjuvant in said emulsion concentrate is from 10 to 70% by weight, in particular from 15 to 50 wt %, based on the total weight of the composition.

The present invention further relates to a method for preparing the inventive composition comprising contacting the pesticide and the base. Usually, the contacting takes place when preparing an agrochemical formulation by known means. The contacting of the components may be achieved by conventional equipment at any temperature, such as room temperature. Preferred mixing methods are those which are applied to prepare agrochemical compositions.

The present invention further relates to a method for preparing an aqueous tank-mix comprises the steps of
a) providing a composition containing the pesticide;
b) providing a composition containing the base; and
c) contacting water and the compositions of steps a) and b).

The present invention further relates to a method for preparing an aqueous tank-mix comprises the steps of
a') providing a composition containing the pesticide and the base;
c') contacting water and the composition of steps a').

Preferably, the composition of step a) is an emulsion concentrate (EC), in particular an emulsion concentrate as described above.

The present invention further relates to a use of the base for increasing the stability of the pesticide of formulae I or II. The stability of the pesticide may be analyzed storage for 14 days at 65° C. An increase of the stability of the pesticide may be identified by analyzing the chemical recovery after said storage.

Advantages of the present invention are for example, that the composition according to the invention has increased stability and that it may be stored longer without decrease of the active compound, even at elevated temperatures. Apart from that, the compositions of the invention have high pesticidal activity, in particular if in the form of an EC which contains an adjuvant.

EXAMPLES

Insecticide A: Pesticide of formula (I).
Alcohol alkoxylate A: linear $C_{16}/C_{18}$ alcohol, ethoxylated and propoxylated, liquid at room temperature, wetting power by immersion: at least 240 s (according to DIN 1772 at room temperature at 1 g/L in 2 g/l sodium carbonate), water content 5-10 wt %, surface tension: 30-35 mN/m (according to DIN 14370 at room temperature at 1 g/L), pH in water about 7.

Example 1—Stabilizing of Emulsion Concentrate

An emulsion concentrate (EC A) having the following composition was prepared from 5.0 wt % Insecticide A, 14 wt % polyarylphenyl ether sulfate ammonium salt, 11.5 wt % ethoxylated iso-C13 alcohol (surface tension 27-29 mN/m according to DIN 53914, at 1 g/l at 23° C. in distilled water), 20 wt % Alcohol alkoxylate A, 10.5 wt % 2-heptanone, and 39 wt % heavy aromatic solvent naphtha (initial boiling point 240° C.). The EC were prepared by following procedure: Insecticide A was first dissolved in 2-heptanone and solvent naphtha with good agitation. After that, the other formulation additives were added into the above solvent solution and mixed until a clear solution of EC A (200 g) was obtained.

a) EC B with Stabilizer A:
30 g of EC A was weighted out in a separated container, and back added 0.201 g of N,N,N'',N''-Tetrakis(2-hydroxypropyl) ethylenediamine (Stabilizer A) and mixed well until uniformly. This emulsion concentrate EC B comprised 0.66 wt % of Stabilizer A.

b) EC C with Stabilizer B:
30 g of EC A was weighted out in a separated container, and back added 0.708 g Stabilizer B (ethoxylated tallow amine, about 20 mol EO) and mixed well until uniformly. The resulting EC C comprised 2.3 wt % Stabilizer B.

Finally, all samples of the emulsion concentrates were stored at 65° C. up to 2 weeks, and chemical assay was determined before and after storage. The chemical stability results as well as initial formulation pH (measured at 1% formulation dilution in water at room temperature) were listed in Table 1. It was found that by addition of Stabilizer A, the chemical stability of Insecticide A was dramatically improved and chemically stable.

TABLE 1

| Chemical recovery of Insecticide A after storage at 65° C. | | | |
|---|---|---|---|
| EC | pH | 4 days | 14 days |
| A[a] | 5.64 | 0% | — |
| B | 7.30 | 100% | 100% |
| C | 7.18 | 100% | 100% |

[a]comparative, not according to the invention.

We claim:
1. An agrochemical composition comprising a pyripyropene pesticide of formula I

Formula I

[Chemical structure of Formula I]

and a base, which is selected from the group consisting of N,N,N',N'-Tetrakis(2-hydroxypropyl)ethylenediamine and a compound of the formula III $$R^2-N\begin{matrix}(A-O)_m-H\\ \\R^1\end{matrix}$$ (III)

where
$R^1$ is a radical $(A-O)_nH$,
A is $C_2-C_4$-alkandiyl,
m is an integer from 1 to 50;
n is an integer from 1 to 50, and
$R^2$ is $C_8-C_{24}$ alkyl or $C_8-C_{24}$ alkenyl.

2. The composition according to claim 1, wherein the concentration of the base is selected from such a range that after dilution of the composition to a concentration of 1.0 wt % in water a pH of at least 7.0 results.

3. The composition according to claim 1, where the concentration of the base is in the range from 0.1 to 10 wt %, based on the total weight of the composition.

4. The composition according to claim 1, wherein the composition comprises no more than 5 wt % water.

5. The composition according to claim 1, wherein the base has solubility in water of at least 0.1 g/l at 20° C.

6. The composition according to claim 1, wherein the composition comprises at least 40 wt % water and the base has solubility in water of at least 1.0 g/l at 20° C.

7. The composition according to claim 1, wherein the base is selected from bases in which a mixture of the base with water at a concentration of 0.1 mol/l has a pH of at least 7.0 in water at 20° C.

8. The composition according to claim 1, where the base is selected from a compound of the formula III $$R^2-N\begin{matrix}(A-O)_m-H\\ \\R^1\end{matrix}$$ (III)

9. The composition according to claim 1, further comprising at least one alkoxylated aliphatic alcohol.

10. The composition according to claim 9, wherein the alkoxylated aliphatic alcohol is selected from one or more compounds of the formula (IV)

$$R^a-O-(C_mH_{2m}O)_x-(C_nH_{2n}O)_y-(C_pH_{2p}O)_z-R^b \quad (IV)$$

in which
$R^a$ represents $C_5-C_{36}$-alkyl or $C_5-C_{36}$-alkenyl;
$R^b$ represents H or $C_1-C_{12}$-alkyl;
m, n and p represent, independently of one another, an integer from 2 to 16;
x, y, and z represent, independently of one another, a number from 0 to 100; and
x+y+z corresponds to a value from 1 to 100.

11. The composition according to claim 10, wherein $R^a$ represents a linear $C_5-C_{36}$-alkyl or $C_5-C_{36}$-alkenyl.

12. The composition according to claim 10, wherein $R^a$ represents a linear $C_{14}-C_{36}$-alkyl or $C_{14}-C_{36}$-alkenyl.

13. The composition according to claim 10, wherein m, n, and p represent, independently of one another, an integer from 2 to 5.

14. The composition according to claim 10, wherein x+y+z corresponds to a value from 10 to 30.

15. The composition according to claim 9, wherein the pesticide is present in dissolved form.

16. The composition according to claim 9, which is an emulsion concentrate.

17. The composition according to claim 1, wherein the base is selected from the group consisting of N,N,N',N'-tetrakis(2-hydroxypropyl)ethylenediamine and a compound of formula III, wherein the compound of formula III is an ethoxylated $C_{12-20}$ fatty amine selected from the group consisting of ethoxylated coco amine, ethoxylated oleyl amine, ethoxylated tallow amine, and ethoxylated stearyl amine.

18. The composition according to claim 1, wherein the pesticide is present in dissolved form.

19. The composition according to claim 1, wherein the pesticide is present as an emulsion concentrate.

20. A method for preparing the composition as defined in claim 9, comprising contacting said pesticide and said base.

21. A method for protecting plants from attack or infestation by insects, acarids or nematodes comprising contacting the plant, or the soil or water in which the plant is growing, with a composition of claim 1 in pesticidally effective amounts.

22. A method for controlling insects, arachnids or nematodes comprising contacting an insect, acarid or nematode or their food supply, habitat, breeding grounds or their locus with a composition according to claim 1 in pesticidally effective amounts.

23. A method for protection of plant propagation material comprising contacting the plant propagation material with a composition as defined in claim 1 in pesticidally effective amounts.

24. Seed treated with the composition according to claim 1.

25. A method for preparing an aqueous tank-mix comprising
a) providing a composition containing a pesticide of formula I Formula I

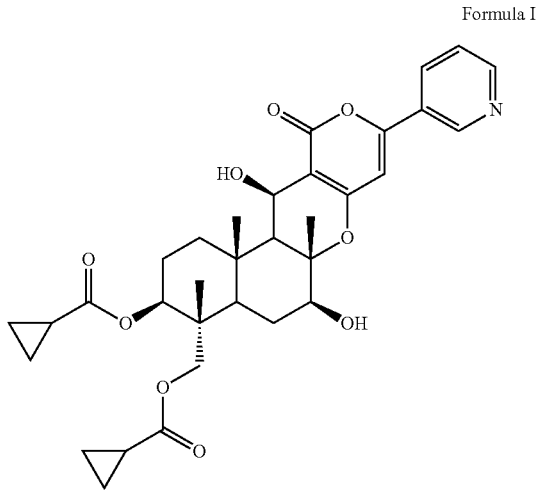

b) providing a composition containing a base, which base is characterized by an acidity constant of the conjugate acid of at least 7.0, determined in water at 20° C., and which is selected from the group consisting of N,N,N',N'-Tetrakis(2-hydroxypropyl)ethylenediamine and a compound of formula III

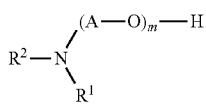
(III)

where
$R^1$ is a radical $(A-O)_nH$,
A is $C_2-C_4$-alkandiyl,
m is an integer from 1 to 50,
n is an integer from 1 to 50, and
$R^2$ is $C_8-C_{24}$-alkyl or $C_8-C_{24}$-alkenyl;
and
c) contacting water and the compositions of steps a) and b).

26. Kit of parts comprising, as separate components, a) a pesticide of formula I Formula I

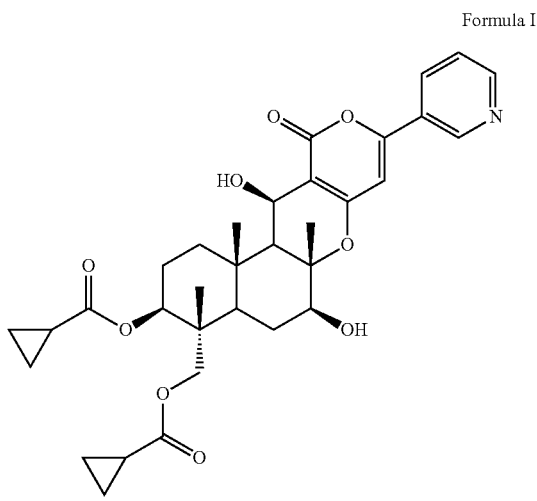

and b) a base characterized by an acidity constant of the conjugate acid of at least 7.0, determined in water at 20° C., and which is selected from the group consisting of N,N,N',N'-Tetrakis(2-hydroxypropyl)ethylenediamine and a compound of formula III

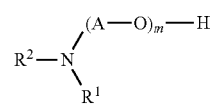
(III)

where
$R^1$ is a radical $(A-O)_nH$,
A is $C_2-C_4$-alkandiyl,
m is an integer from 1 to 50,
n is an integer from 1 to 50, and
$R^2$ is $C_8-C_{24}$-alkyl or $C_8-C_{24}$-alkenyl, for combined use.

27. A method of increasing the stability of an agricultural composition comprising a pyripyropene pesticide of formula I:

Formula I

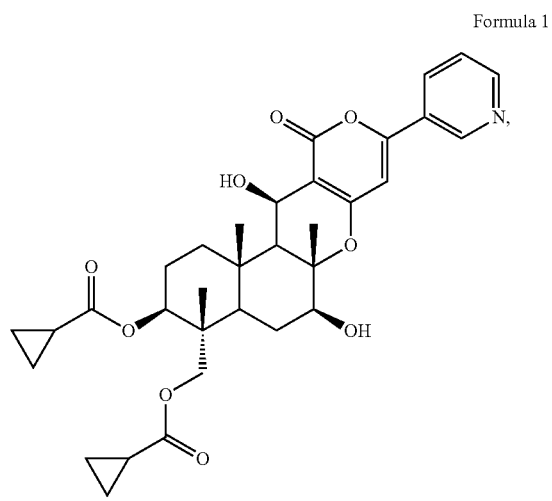

wherein the method comprises contacting said pyripyropene pesticide of formula I with a base in an amount effective to stabilize the pyripyropene pesticide, wherein the base is selected from the group consisting of N,N,N',N'-Tetrakis(2-hydroxypropyl)ethylenediamine and a compound of formula III

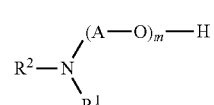
(III)

where
$R^1$ is a radical $(A-O)_nH$,
A is $C_2-C_4$-alkandiyl,
m is an integer from 1 to 50
n is an integer from 1 to 50, and
$R^2$ is $C_8-C_{24}$ alkyl or $C_8-C_{24}$ alkenyl.

* * * * *